United States Patent [19]
Svensson

[11] Patent Number: 5,299,787
[45] Date of Patent: Apr. 5, 1994

[54] GAS-SPRING WITH AN ADJUSTABLE DEVICE TO BRAKE AND/OR FIX THE GAS SPRING STROKE

[75] Inventor: Rolf B. B. Svensson, Vimmerby, Sweden

[73] Assignee: Ultra Tan International AB, Vimmerby, Sweden

[21] Appl. No.: 689,870
[22] PCT Filed: Jun. 16, 1989
[86] PCT No.: PCT/SE89/00344
§ 371 Date: Aug. 12, 1991
§ 102(e) Date: Aug. 12, 1991
[87] PCT Pub. No.: WO90/07070
PCT Pub. Date: Jun. 28, 1990

[30] Foreign Application Priority Data
Dec. 12, 1988 [SE] Sweden .................... 8804492

[51] Int. Cl.5 .................... F16F 9/02; F16F 11/00; A61N 5/06
[52] U.S. Cl. .................... 267/64.12; 188/67
[58] Field of Search .................... 267/64.11, 64.12, 196, 267/201, 205, 207; 188/271, 67

[56] References Cited
U.S. PATENT DOCUMENTS

| | | | |
|---|---|---|---|
| 2,237,318 | 4/1941 | Snyder | 267/207 |
| 2,889,895 | 6/1959 | Snow | 188/271 |
| 4,078,778 | 3/1978 | Hubweber | 267/64.12 |
| 4,309,027 | 1/1982 | Molders et al. | 267/64.12 |
| 4,606,442 | 8/1986 | Paton et al. | 188/271 |
| 4,881,723 | 11/1989 | Bauer et al. | 267/64.12 |

FOREIGN PATENT DOCUMENTS

0256390 2/1988 European Pat. Off. .
2540648 3/1977 Fed. Rep. of Germany .
3041937 1/1987 Fed. Rep. of Germany .

Primary Examiner—Matthew C. Graham
Attorney, Agent, or Firm—Nies, Kurz, Bergert & Tamburro

[57] ABSTRACT

A gas-spring arrangement includes a gas-spring which has a substantially tubular, external casing (2) and a rod (3) which is guided for axial movement in the casing, between two terminal positions and is dampened by means of gas constrictions. The gas-spring includes attachment links at each end for attachment of the gas-spring between mutually movable devices or structures, such as a pivoted hood on a sunbed. The gas-spring arrangement includes a friction device (6) which is operative to brake the relative axial movement between the gas-spring casing (2) and the gas-spring rod (3), and also to fix the casing (2) and the rod (3) in selective relative positions, i.e., positions between the terminal positions, and when combined with a hooded sunbed, can maintain the hood in a desired raised position.

11 Claims, 3 Drawing Sheets

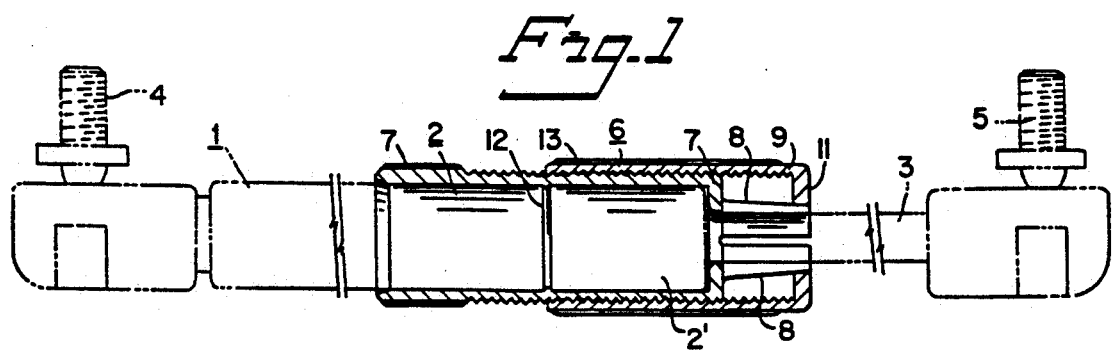
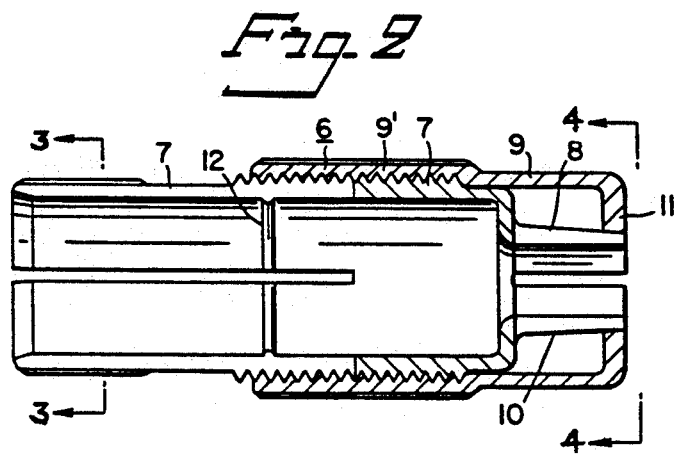
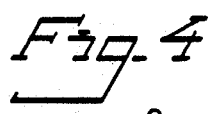
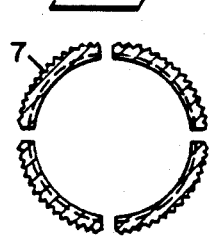
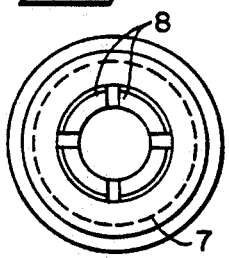
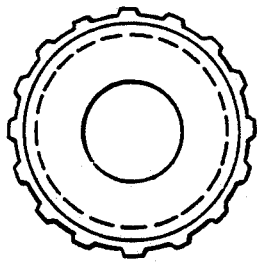
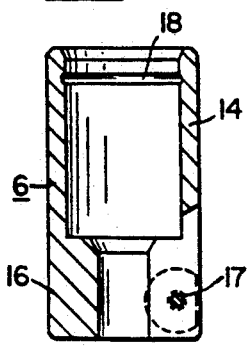
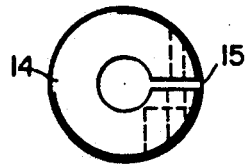
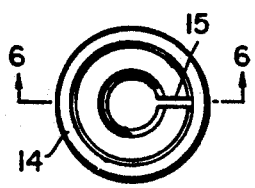

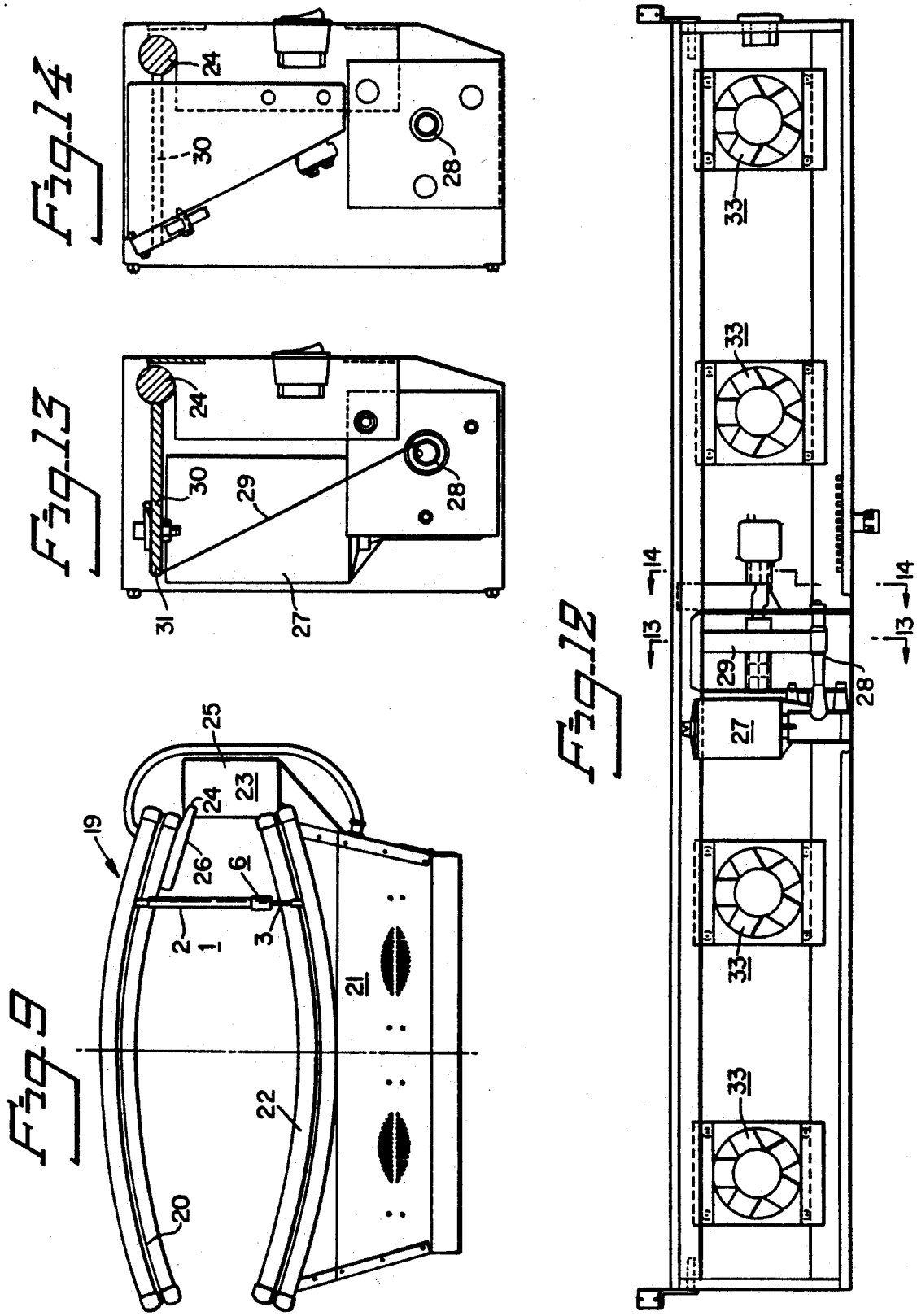

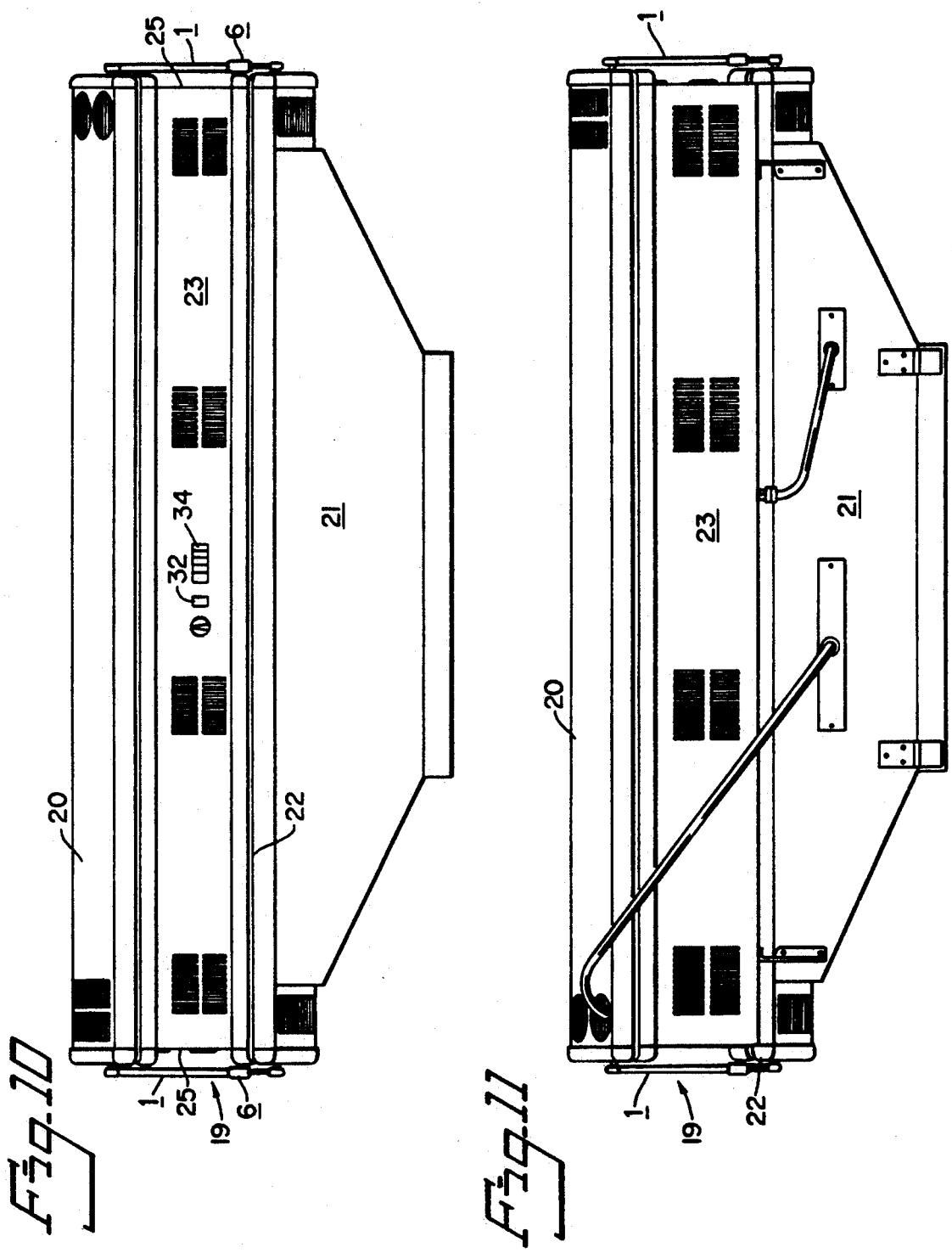

GAS-SPRING WITH AN ADJUSTABLE DEVICE TO BRAKE AND/OR FIX THE GAS SPRING STROKE

The present invention pertains to a gas-spring arrangement in which the so-called gas spring includes a substantially tubular outer casing and a rod which is guided for axial movement in the tubular casing, between two terminal positions and is dampened with the aid of gas constrictions, and further includes means for attachment of the gas spring.

BACKGROUND OF THE INVENTION

Gas springs are used, inter alia, to dampen the relative movement between two movable parts. One example of such use is found in so-called sun-bed constructions in which the upper part, or canopy, of the bed structure can be moved between a position in which the canopy lies essentially contiguous with the bottom part of said structure, i.e. the bed surface, and an upwardly swung position, in which the canopy is positioned at an angle to the bed surface.

SUMMARY OF THE INVENTION

The present invention relates to a gas-spring arrangement which enables the gas-spring to be secured readily and detachably in selected locations between said terminal positions, therewith obviating the need to provide separate, complicated stop and fixating devices, among other things.

The invention thus relates to a gas-spring arrangement in which the so-called gas-spring includes a substantially tubular outer casing, a rod which is guided for axial movement in the casing between two terminal positions and is dampened with the aid of gas constrictions, and which further includes means for attaching the gas-spring between devices or structures capable of movement therebetween. The gas-spring arrangement is particularly characterized in that it includes a friction device which is operative to brake or retard the relative axial movement of the casing and the rod and also to fixate the casing and rod in selective relative positions, essentially positions located between terminal positions of extension and retraction of the gas-spring.

BRIEF DESCRIPTION OF THE DRAWINGS

The invention will now be described in more detail with reference to exemplifying embodiments thereof and also with reference to the accompanying drawings, of which FIG. 1 illustrates schematically a first embodiment of an inventive arrangement, and shows the friction device in axial section;

FIG. 2 is an axial sectional view of a friction device substantially according to FIG. 1;

FIG. 3 is a sectional view taken on the line 3—3 in FIG. 2;

FIG. 4 is an end view of the friction device housing looking in the direction of 4—4 in FIG. 2;

FIG. 5 is and end view of the sleeve of the friction device seen in FIG. 2;

FIG. 6 is a schematic axial sectional view taken on line 6—6 according to of FIG. 8, through a second embodiment of the inventive arrangement;

FIG. 7 shows the arrangement illustrated in FIG. 6 from beneath;

FIG. 8 shows the arrangement illustrated in FIG. 6 from above;

FIG. 9 illustrates schematically an inventive gas-spring arrangement fitted to a sun-bed construction provided with an electric hoist arrangement for movement of the canopy part of the sun-bed, said sun-bed being seen in its longitudinal direction;

FIG. 10 shows the sun-bed of FIG. 9 from the left in said Figure;

FIG. 11 shows the sun-bed of FIG. 9 from the right in said Figure;

FIG. 12 illustrates schematically a sun-bed panel construction as shown in FIG. 11, but without a back-piece;

FIG. 13 is a schematic sectional view taken on 13—13 of FIG. 12; and

FIG. 14 is a schematic sectional view taken on 14—14 of FIG. 12.

DESCRIPTION OF THE PREFERRED EMBODIMENTS

In FIG. 1, the reference 1 identifies a gas-spring which is shown in chain lines and which includes a substantially tubular, outer casing 2, a rod 3 which is guided for axial movement into and out of the hollow casing 2, between two terminal positions and is dampened herewith by means of gas constrictions (not shown), said gas-spring further including attachment parts 4, 5 for attachment of the gas-spring between relatively movable devices or structures, not shown.

FIGS. 1 and 2-5 illustrate an embodiment of a friction device 6 which is effective in braking or retarding the relative axial movement of the casing 2 and the rod 3, and the device, in appropriate circumstances, can be used to fixate the casing and the rod in selective relative positions, substantially positions located between said terminal positions. The illustrated friction device comprises a housing 7 which is intended to be fitted externally onto the gas-spring casing 2, preferably at one end 2', and held firmly in position at said one end, and includes clamping members 8 arranged around the rod 3 and connected to said housing, these clamping members preferably being intended to be brought into clamping engagement with the rod 3, with the aid of screw-type devices. In the case of the illustrated embodiment, the screw devices comprise a nut arrangement 9 which coacts with the outer face 7' of the housing through the intermediary of the screwthreads 9'. The illustrated nut arrangement is such that when said nut arrangement is screwed toward the housing and unscrewed therefrom, the clamping members will generate continuous, variable clamping forces, for example through the intermediary of conical faces 10. In the case of the illustrated embodiment, the clamping members 8 define a substantially cylindrical configuration around the rod 3, and are slightly conically shaped externally, wherewith the clamping members will be displaced radially to a given extent by means of axially movable ring-part 11 on the nut arrangement 9, these ring-part acting externally on the clamping members. The illustrated clamping members 8 comprise four mutually identical parts separated by axially extending slots.

The housing 7 has an internal flange 12 which coacts with a corresponding groove 13 in the casing, such as to enable the housing to be snapped firmly into engagement with the casing.

Illustrated in FIGS. 6–8 is an embodiment in which a housing 14 is intended to be fitted externally to the casing 2 and firmly secured thereto. A radial slot 15 extends axially along the housing 16, to form housing parts or clamping parts 16 extending substantially around the rod 3, wherewith a screw 17 or some like device is provided for increasing or decreasing the width of the slot 15 such as to vary continuously the clamping forces exerted by the clamping parts 16. This embodiment is also provided with an internal flange, referenced 18, corresponding to the aforedescribed flange 12 of the FIG. 1 embodiment.

FIGS. 9–14 illustrate schematically a sun-bed 19. The upper part or canopy 20 of the sun-bed is raised and lowered with the aid of an electric hoist arrangement which is complemented with the inventive gas-spring arrangements, such as the gas-spring illustrated in FIG. 1. The gas-spring arrangements are primarily intended to replace the hoist arrangement as canopy positioning means during breakdowns in operation. The sun-bed of the illustrated embodiment includes a box-like base 21, a lower part 22 which rests on the base 21, an upright panel construction 23 which is mounted on the base 21, the lower part 22 and the canopy 20, said canopy being rotatably journalled on the panel 23 for pivotal movement towards and away from the lower bed part.

As will be seen from FIGS. 12–14, the major part of the hoist arrangement is located in the panel. The reference 24 identifies a rotational shaft which is rotatably journalled in the panel structure and extends through and along said panel structure and which is connected with the canopy 20, preferably externally of the side walls 25 of said panel, for swinging of the canopy, e.g., with the aid of end parts 26 extending transversely of the shaft 24. The shaft 24 is rotated by means of an electric motor 27, via a winding shaft 28 rotated by means of said motor, a winding element 29, such as a belt or strap 29, arranged between the shaft 28 and an auxiliary arm 30 projecting transversely to the shaft 24 and intended to be wound onto and unwound from said shaft, so as to shorten or lengthen, respectively, the free belt lengths between the shaft and an outer part 31, such as an end part 31, of the auxiliary arm 30, such as to rotate the shaft 24. Thus, when a canopy raise-pulse is delivered to the motor, preferably by a control means 32 on the panel, the hoist arrangement will function to wind the belt or strap 29 onto the shaft 28, so as to swing the auxiliary arm 30 and rotate the shaft 24, and therewith raise the canopy 19. When the motor receives a canopy lowering pulse, through the aforesaid control means 32, the belt or strap is unwound from the shaft and the canopy lowers gravitationally, under its own weight. Although not shown, position limit switches are provided for defining the highest and lowest level to which the canopy can move.

In order to enable the canopy to be manoeuvered and positioned without the aid of the electric hoist arrangement, two gas-spring arrangements are mounted between the canopy and the lower bed part, one at each end wall of the sun-bed and preferably relatively close to said panel structure. The gas-spring is referenced 1 and the friction device is referenced 6. When the electric hoist arrangement is in active use, the gas-spring arrangements are adjusted to a non-friction mode. Adjustment of the gas-spring arrangements to "manual" will enable the canopy of the sun-bed to be lowered manually to its lowermost position and then raised to a position substantially midway between the lowest and the highest canopy positions, the friction device of respective gas-spring arrangements being adjusted so that the canopy is braked and the weight of said canopy counter-balanced, such that said canopy will remain in its manually adjusted position unless acted upon by forces other than those generated by its own weight.

The control panel structure 23 preferably also incorporates four fans 33, with individual controls 34, for blowing ventilating air onto the sun-bed and also houses a timer, control means for automatic cooling of the sun-bed, and the requisite cables.

The method of operation of the inventive arrangement will be understood in all essentials from the aforegoing. Through the intermediary of the continuous, variable clamping forces generated by the friction device, it is possible to achieve a desired braking force with respect to mutual movement between the casing 2 and the rod 3. The braking force can be increased to an extent such as to lock the casing and the rod relative to one another.

It will be understood from the aforegoing that the invention affords important advantages in the form, inter alia, of increased flexibility when using gas-springs, and also novel possibilities of use.

The invention has been described in the aforegoing with reference to an exemplifying embodiment thereof. It will be understood, however, that modifications and minor changes can be made, without departing from the scope of the inventive concept.

For instance, embodiments are conceivable in which the friction device is attached to the rod 3 instead of the casing 2 and has clamping members or the like which act on said casing. The clamping members may be located externally, as with the clamping members 8, 16, or internally, wherewith radially displaceable parts are arranged to act against the inner wall or corresponding surface of the casing, such as to achieve braking of relative movement between the casing and the rod, and when appropriate to lock or fixate said casing rod against relative movement.

When the friction device is attached to the casing, the clamping members acting against the rod may be located inside the casing 2 instead of outside the casing as, for instance, in accordance with FIG. 1.

It will be understood, that when using the embodiment illustrated in FIGS. 9–14, the construction of both the gas-spring arrangement and the hoist arrangement can be varied.

Consequently, the invention is not restricted to the aforedescribed embodiments but modifications can be made within the scope of the following claims.

What is claimed and desired to be secured by Letters Patent is:

1. A gas-spring arrangement comprising a substantially tubular, outer casing, a rod which is guided for axial movement in the casing between two terminal positions and dampened through the action of gas constrictions, and further including attachment means on said rod and on said casing for attaching the gas-spring between mutually movable devices, said gas-spring arrangement further including an adjustable friction clamp device (6) which is secured on said gas spring and engages both of said rod and said casing and is operative to brake the relative axial movement between the casing (2) and the rod (3) and also can be adjusted to fix the casing (2) and the rod (3) relative to one another in any of a multiplicity of desired selected positions, at and between said terminal positions.

2. An arrangement according to claim 1, wherein means secure the friction device (6) to the casing (2) and said friction clamp device includes clamping means (8, 16) which engage and clamp against the rod (3), to fix said rod relative to said casing.

3. An arrangement according to claim 1, wherein means secure said friction device (6) to the rod (3) and said friction clamp device includes clamping means which engage against the casing (2) to fix said casing relative to said rod.

4. A gas-spring arrangement comprising a substantially tubular, outer casing, a rod which is guided for axial movement in the casing between two terminal positions and dampened through the action of gas constrictions, and further including attachment means on said rod and on said casing for attaching the gas-spring between mutually movable devices, said gas-spring arrangement further including an adjustable friction device (6) which is secured on said gas spring and engages both of said rod and said casing and is operative to brake the relative axial movement between the casing (2) and the rod (3) and also can be adjusted to fix the casing (2) and the rod (3) relative to one another in desired selected positions, between said terminal positions; said friction device (6) comprising a housing (7) with a cylindrical part fitted externally over the casing (2) of the gas spring, and said casing and said cylindrical part include cooperative means securing said friction device firmly on said casing; and said friction device further comprising clamping means (8; 16) connected to the housing (7) and disposed around said rod (3), and screw means connected to said clamping means to move said clamping means into selectively adjustable clamping engagement with said rod, by screwing said screw means.

5. An arrangement according to claim 4, wherein an integral part of said housing comprises said clamping means which has a radially and axially extending slot (15), and said screw means (17) is in said integral part of said housing adjacent said clamping means slot and is operative to vary the width of said slot (15) to generate continuous, selectively variable clamping forces by said clamping means on said rod.

6. An arrangement according to claim 4, wherein said screw means includes a nut and threads on said housing whereby said nut can be screwed and unscrewed on said housing (7) to thereby generate continuous, selectively variable clamping forces on said rod by said clamping means.

7. An arrangement as defined in claim 6, wherein said clamping means are an annular group of spaced-apart fingers with conical outer surfaces converging from the housing toward said rod and said nut has a ring part encircling said conical fingers and movable back and forth along said fingers as said nut is screwed back and forth respectively on the threads on said housing.

8. A sun-bed construction with two long sides and two ends comprising: an elongate bed base part; an elongate canopy (20) and a means pivotally securing one long side of said canopy to a long side of said bed base part; said canopy having sun-bed radiation sources fitted thereto; and said canopy being journalled by said pivotal means for rotation about the axis of a longitudinal rotational shaft (24) located at said long side of said bed base part, pivotal movement of said canopy being provided by a powered hoist means; and a gas-spring arrangement connected between said canopy and said bed base part including means enabling holding of said canopy in a desired pivoted position relative to said bed base part; said gas-spring arrangement including: at least one gas spring with a substantially tubular, outer casing, a rod which is guided for axial movement in said casing between two terminal positions and dampened through the action of gas constrictions in the gas spring, and further including attachment means on said casing and on said rod which connect the gas-spring between mutually movable parts on said canopy and said bed base part, and wherein said gas-spring arrangement further includes an adjustable friction clamp device (6) secured on said at least one gas spring and which engages both the rod and the casing of said gas spring and is operative to brake the relative axial movement between the casing (2) and the rod (3) of said gas spring and can also be adjusted to fix the casing (2) and the rod (3) relative to one another in any of a multiplicity of desired selected positions, at and between said terminal positions.

9. A sun-bed construction according to claim 8, wherein the sun-bed construction is provided with two said gas-springs, one at each end of the sun-bed construction, each gas-spring being arranged to function between the canopy (20) and the bed base part (22) of the sun-bed.

10. A sun-bed construction according to claim 8, wherein the canopy (20) is carried by a longitudinally extending panel structure (23) which is mounted adjacent and between one long side of the canopy and one long side of the bed base part of said sun-bed.

11. A sun-bed construction according to claim 8, wherein a longitudinally extending, rotatably journalled shaft (24) is connected to said canopy to effect pivoting movement of said canopy, and an electric motor (27) with a winding shaft (28) driven by said motor, and a winding element (29), arranged between the winding shaft (28) and an auxiliary arm (30) on and projecting transversally to the journalled shaft (24), and which is intended to rotate said journalled shaft when the winding shaft is rotated by said motor.

* * * * *